United States Patent [19]

Nakanishi

[11] Patent Number: 4,460,341
[45] Date of Patent: Jul. 17, 1984

[54] DENTAL HANDPIECE

[75] Inventor: Toshimasa Nakanishi, Kanuma, Japan

[73] Assignee: Nakanishi Dental Mfg. Co., Ltd., Kanuma, Japan

[21] Appl. No.: 422,441

[22] Filed: Sep. 23, 1982

Related U.S. Application Data

[63] Continuation of Ser. No. 342,918, Jan. 26, 1982, abandoned.

[30] Foreign Application Priority Data

May 8, 1981 [JP] Japan ................................. 56-70007

[51] Int. Cl.³ ............................................. A61C 3/03
[52] U.S. Cl. ...................................................... 433/122
[58] Field of Search ................................ 433/122, 125

[56] References Cited

U.S. PATENT DOCUMENTS 2,135,933  11/1938  Blair ........................................ 422/122
3,149,494   9/1964  Hulse ........................................ 74/47
4,341,519   7/1982  Kuhn et al. ............................. 433/122

*Primary Examiner*—Robert Peshock
*Attorney, Agent, or Firm*—Wenderoth, Lind & Ponack

[57] ABSTRACT

A dental handpiece having a handle portion, a powerhead assembly integrally and perpendicularly linked to the handle portion, a holding sleeve fixedly inserted in the handle portion, a driving shaft journaled in a bushing in the holding sleeve, the driving shaft including an integral disc at its outer end, the outer end surface of the integral disc being concave, the concave surface carrying at its periphery a guide pin which is directed toward the point of intersection of the axis of the driving shaft and that of a cylindrical hollow driven shaft having a spherical middle portion, the cylindrical driven shaft being rotatably mounted in the powerhead assembly in bushings, the spherical middle portion of the cylindrical driven shaft having a longitudinal concave guide slot and the guide pin being slidably inserted into the longitudinal concave guide slot to couple the driving shaft with the cylindrical driven shaft, and a dental tool on the cylindrical driven shaft, whereby the dental tool is driven so as to rotate in one direction and in the opposite direction alternately by the circular rotation of the driving shaft.

2 Claims, 3 Drawing Figures

DENTAL HANDPIECE

This is a continuation application of application Ser. No. 342,918, filed Jan. 26, 1982, now abandoned.

BACKGROUND OF THE INVENTION

This invention relates to improvements in a dental handpiece for the treatment of root canals, and more particularly in a dental handpiece for the enlarging of root canals.

For the treatment and in particular for enlarging of root canals, a dental tool must be driven to rotate alternately in one direction and in the other direction.

In a conventional dental handpiece such as disclosed in the specification of U.S. Pat. No. 3,578,745, a driving Utility Model Application Publication No. 386/1977, a driving shaft rotatably held in a sleeve has an end disc which carries at its periphery a guide pin, and perpendicularly to the axis of the driving shaft, and in the interior of the case of a dental tool is mounted a hollow cylinder having a longitudinal guide slot therein. The hollow cylinder is integral with the tool, and the guide pin engages in the guide slot so as to slide reciprocally in the guide slot when the disc rotates continuously. Through the continuous rotation of the disc, reciprocating rotary movement is achieved around the axis of the cylinder so that the dental tool rotates reciprocally through about one quarter of a turn.

It has been found, however, that when the guide pin is slidably coupled in the longitudinal guide slot of the cylinder it can not deliver effective rotating driving power to a dental tool and may disengage from of the guide slot at the two extreme positions thereof. In addition, the alternate rotational is small and it is impossible to increase the oscillating angle longitudinal guide slot and the pinion lug, thus causing a backlash.

Moreover, the oscillating angle of the dental tool has been narrowed and also it is impossible to widen the oscillating angle to more than 70°.

A principal object of this invention is to provide a dental handpiece for the treatment of root canals whereby dental tools such as buffers, drills, reamers or the like can be effectively driven to rotate alternately in one direction and in the other direction.

Another object of this invention is to provide a dental handpiece for the treatment of root canals including a driving shaft and a cylindrical driven shaft having a spherical middle portion and a guide pin provided at the periphery of a concave outer end surface of an end disc of the rotating driving shaft slidably engaged in a longitudinal concave guide slot in the cylindrical driven shaft.

Another object of this invention is to provide a dental handpiece for the treatment of root canals in which a wide oscillating angle of a dental tool can be achieved so as to achieve effective oscillatory movement for the dental tool.

A further object of this invention is to provide a dental handpiece for the treatment of root canals whereby backlash between the driving shaft and the cylindrical driven shaft can be prevented in order to assure smooth operation of the dental tool of the dental handpiece.

A still further object of this invention is to provide a device which will enable the dentist to carry out operation of the handpiece with tactile sense of his fingers.

A still further object of this invention is to provide a device suitable for the aforementioned purposes which will have a comparatively simple construction and at the same time be sufficiently rigid, strong and durable.

BRIEF DESCRIPTION OF DRAWINGS

While I have shown in the accompanying drawings, a preferred embodiment of my invention, it should be understood that the same is susceptible of modification and change without departing from the spirit of my invention.

DETAILED DESCRIPTION

Figure 1:
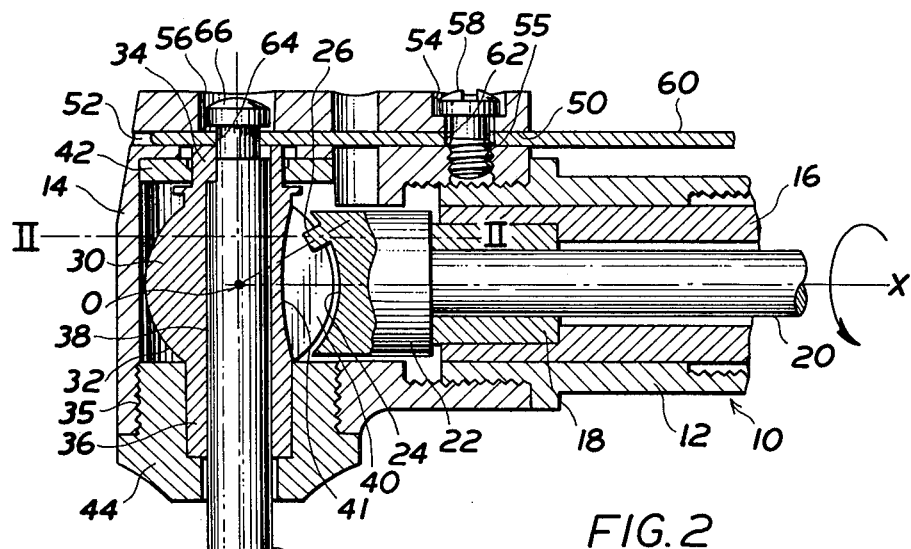
FIG. 1 is a fragmentary enlarged vertical sectional view of an embodiment of the dental handpiece according to preferred embodiment of this invention.
Figure 2:
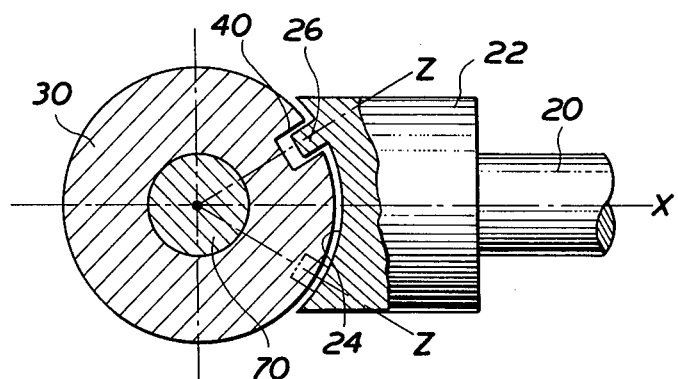
FIG. 2 is a partial cross sectional view, on an enlarged scale, taken along a line II—II of FIG. 1, particularly showing the driving shaft coupled with the cylindrical driven shaft.
Figure 3:
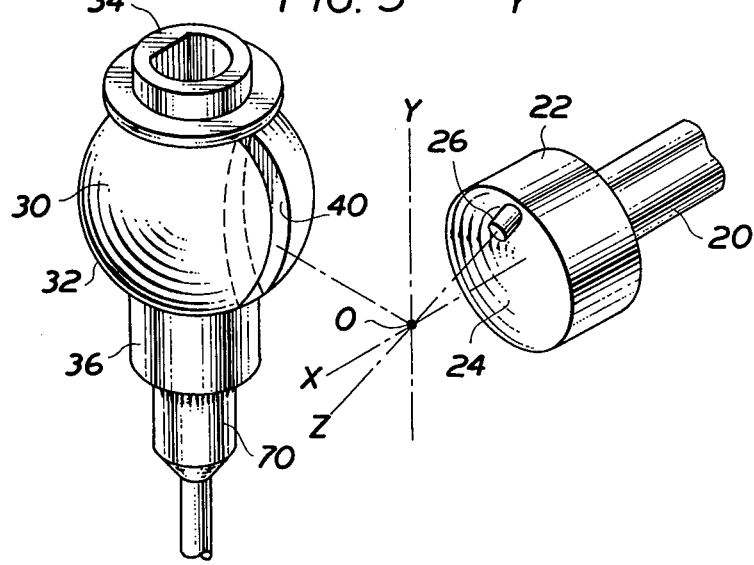
FIG. 3 is an enlarged exploded perspective view of a driving shaft and the cylindrical driven shaft, showing the point of intersection of the central axis X of the driving shaft and the central axis Y of the driven shaft.

Referring to FIGS. 1, 2 and 3, the preferred embodiment which has been selected to illustrate this invention comprises a dental handpiece 10 including a handle portion 12 and a powerhead assembly 14 which is integrally connected to the handle portion.

Fixedly mounted in the handle portion 12 of the dental handpiece 10 is a holding sleeve 16, in which a rotating driving shaft 20 having an integral end disc 22 at its outer end portion is rotatably journalled in a bushing 18 in the holding sleeve 16. As particularly shown in FIGS. 1 and 2, the outer end surface 24 of the end disc 22 is spherically concave complementary to the surface of a spherical middle portion 32 of a hollow cylindrical driven shaft 30 having the axis of rotation Y thereof perpendicular to the axis of rotation X of driving shaft 20. A guide pin 26 is provided at a peripheral edge of the concave end surface 24 and is directed at the point of intersection O of axis X of the driving shaft 20 and axis Y of the cylindrical driven shaft 30 when they are coupled with each other.

The upper end portion 34 and the lower end portion 36 of shaft 30 are rotatably mounted in the powerhead assembly 14 and a bushing cap 44 respectively.

A central longitudinal bore 38 extends axially through a substantial length of the driven shaft 30, and has a dental tool 70 fixed therein, and a guide slot 40 extends along the spherical extend through a substantial of the driven shaft 30, surface of the middle portion 32 parallel to said bore 38 and in which the guide pin 26 is engaged to connect the driving shaft 20 to the driven shaft 30.

The bottom 41 of the longitudinal guide slot 40 is concavely shaped so that the other end portion of the guide pin 26 does not come into contact with the bottom of the guide slot 40.

The cylindrical driven shaft 30 is rotatably mounted in the powerhead assembly 14 at its upper end 34 in a bushing 42 and at its lower end 36 in the bushing cap 44 respectively. The bushing cap 44 is threaded into threads 35 around the inner end periphery of the powerhead assembly 14, so that the guide pin 26 is slidable in the concave guide slot 40 during rotation of the shaft 20 to couple the driven shaft 30 with the driving shaft 20.

In this way, the guide pin 26 when driven is caused to slide alternately or reciprocally in the concave guide slot 40 when the end disc 22 rotates continusouly, thus producing alternate reciprocal rotation within a given angle of oscillation of the dental tool 70.

Slits 50 and 52 are provided in a top portion of the handle portion 12 and extending parallel to the driving shaft 20, and a pair of bores 54 and 56 are provided which extend vertically across the slits 50 and 52 respectively, the bore 56 being aligned with the central bore 38 of the driven shaft 30. A thread 55 is formed in the lower inner periphery of the bore 54.

A locking plate 60 having a pair of openings 62 and 64 to coincide with the respective bores 54 and 56 is slidably inserted into the slits 50 and 52. A screw 58 is inserted into the opening 62 and the grooved bore 54 to fix the locking plate 60.

Fixedly held in the longitudinal central opening 38 is the dental tool 70, which is fastened by a screw 66 extending into the bore 56, an opening 64 and a grooved opening (not shown) formed in a top portion of the dental tool 70 so that the dental tool can be kept at a right angle to the axis X of the driving shaft 20. Accordingly, the dental tool 70 is prevented from slipping down along the axis of the driven shaft 30 and becoming disengaging therefrom.

As shown in the drawings, the center line Z of the guide pin 26 on the disc 22 is directed toward the point O of intersection of the axis Y of the driving shaft 20 and the axis X of the driven shaft 30, the point of intersection being also the center of the sphere 32 on the driven shaft 30.

The continuous rotation of the driving shaft 20 in one direction provides alternate rotary motion of the shaft 38 around the axis Y of the driven shaft 30 so that the dental tool 70 is driven so as to rotate horizontally in one direction and in the opposite direction alternately.

In the dental handpiece of this invention, the guide pin 26 on the disc 22 moves within the longitudinal concave guide slot 40 and is always directed toward the point of intersection O of the axis X of the driving shaft 20 and the axis Y of the driven shaft 30 so that the distance between the outer end of the guide pin 26 and the point of intersection O is always kept constant, thus preventing any possible disengagement of the guide pin 26 at the two extreme end positions in the guide slot 40. In addition, through contact of the guide pin 26 with side faces of the guide slot 40, transmission of the driving power is carried out quite easily and securely and abrasion of the sliding members and parts is rather small.

While one embodiment of the invention has been described, it is obvious that variations and modifications are possible without departing from the invention. It is desired to cover all such forms of the invention as would be apparent to one skilled in the art, and that come within the scope of the appended claims.

I claim:

1. A dental handpiece comprising:
   a handle portion;
   a powerhead assembly integrally connected to said handle portion;
   a driving shaft rotatably journalled in said handle portion for rotation around the longitudinal axis of said driving shaft, said driving shaft having a disc at the outer end thereof with an outer end surface which is spherically concave, said concave end surface having a cylindrical guide pin thereon adjacent the periphery of said surface;
   a hollow driven shaft rotatably mounted in said powerhead assembly for rotation around the longitudnal axis of said driven shaft, said axis of said hollow driven shaft being perpendicular to the axis of said driving shaft, the middle portion of said hollow driven shaft having a surface with a spherical shape complementary in shape to the shape of the concave outer end surface of said disc on said driving shaft, said middle portion having a guide slot in the spherical shape surface defined by straight sides and extending parallel to the axis of rotation of said driven shaft and slidably receiving said guide pin therein for smooth reciprocating sliding motion, said guide pin being directed to the point of intersection of said axis of rotation of said driving shaft and the center of the sphere of which said spherical shape surface forms a part for coupling said driving shaft with said driven shaft; and
   means for holding a dental tool in said hollow driven shaft.

2. A dental handpiece as claimed in claim 1 wherein said powerhead assembly has a slit in the top portion thereof parallel to said driving shaft and at least two bores extending transversely of said slit with one of said bores opening into said hollow driven shaft; and said means for holding the dental tool comprise a locking plate having a pair of openings therein spaced a distance corresponding to the distance between said bores and slidably positioned in said slit, a screw extending in the other of said bores through said locking plate for holding said locking plate in said slit, and a further screw in the one of said bores extending through said locking plate and adapted to engage in the end of a dental tool in said hollow driven shaft for holding the dental tool in said hollow driven shaft.

* * * * *